(12) United States Patent
Niki et al.

(10) Patent No.: US 11,927,490 B2
(45) Date of Patent: Mar. 12, 2024

(54) STICKING-TYPE DEEP BODY THERMOMETER

(71) Applicant: Murata Manufacturing Co., Ltd., Nagaokakyo (JP)

(72) Inventors: Yoshiki Niki, Nagaokakyo (JP); Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 756 days.

(21) Appl. No.: 17/090,273

(22) Filed: Nov. 5, 2020

(65) Prior Publication Data

US 2021/0055168 A1    Feb. 25, 2021

Related U.S. Application Data

(63) Continuation of application No. PCT/JP2019/019848, filed on May 20, 2019.

(30) Foreign Application Priority Data

May 21, 2018    (JP) .................. 2018-097443

(51) Int. Cl.
G01K 13/20    (2021.01)
A61B 5/01    (2006.01)
(Continued)

(52) U.S. Cl.
CPC ............... *G01K 13/20* (2021.01); *A61B 5/01* (2013.01); *G01K 7/16* (2013.01); *G01K 7/427* (2013.01)

(58) Field of Classification Search
CPC .......... G01K 13/20; G01K 7/16; G01K 7/427; A61B 5/01
(Continued)

(56) References Cited

U.S. PATENT DOCUMENTS 9,354,122 B2    5/2016    Bieberich et al.
10,274,383 B2    4/2019    Bieberich et al.
(Continued)

FOREIGN PATENT DOCUMENTS

JP    2009080000 A    4/2009
JP    2009222543 A    10/2009
(Continued)

OTHER PUBLICATIONS

Translation of JP2012154859A (Year: 2012).*
(Continued)

*Primary Examiner* — Mirellys Jagan
(74) *Attorney, Agent, or Firm* — ArentFox Schiff LLP

(57) ABSTRACT

A sticking-type deep body thermometer that includes a thermometer body; a sticking member having an adhesive property on a bottom surface of thermometer body; a first thermal resistor having a predetermined thermal resistance and disposed substantially parallel to the sticking member; a first temperature sensor configured to detect a first temperature at a first surface of the first thermal resistor adjacent to the sticking member; a second temperature sensor configured to detect a second temperature at a second surface of the first thermal resistor opposite the first surface; a deep body temperature detection circuit configured to estimate a deep body temperature based on the first temperature and the second temperature; and an attachment/detachment sensor configured to detect attachment and detachment of the sticking-type deep body thermometer in accordance with a temperature difference between the first temperature and the second temperature and/or a temperature rate of change of the first temperature.

16 Claims, 9 Drawing Sheets

(51) Int. Cl.
  *G01K 7/16* (2006.01)
  *G01K 7/42* (2006.01)
(58) Field of Classification Search
  USPC .......................................................... 374/101
  See application file for complete search history.

(56) References Cited

U.S. PATENT DOCUMENTS

| | | | |
|---|---|---|---|
| 10,830,649 | B2 | 11/2020 | Tsuchimoto |
| 2011/0158284 | A1* | 6/2011 | Goto ...................... G01K 7/427 |
| | | | 374/E13.002 |
| 2012/0289855 | A1 | 11/2012 | Bieberich et al. |
| 2016/0238463 | A1 | 8/2016 | Bieberich et al. |
| 2016/0367150 | A1 | 12/2016 | Koch et al. |
| 2018/0064348 | A1* | 3/2018 | Tsuchimoto .............. G01K 1/16 |
| 2018/0184908 | A1* | 7/2018 | Meyerson ............ A61B 5/6833 |
| 2019/0049317 | A1 | 12/2019 | Tsuchimoto |

FOREIGN PATENT DOCUMENTS

| | | | |
|---|---|---|---|
| JP | 2009229272 | A | 10/2009 |
| JP | 2012154859 | A * | 8/2012 |
| JP | 2012154859 | A | 8/2012 |
| JP | 2012220420 | A | 11/2012 |
| JP | 2014052350 | A | 3/2014 |
| JP | 2014513310 | A | 5/2014 |
| JP | 2016055059 | A | 4/2016 |
| WO | 2016185905 | A1 | 11/2016 |
| WO | 2017183709 | A1 | 10/2017 |

OTHER PUBLICATIONS

Japanese Office Action issued for Japanese Application No. 2020-521217, dated Jul. 6, 2021.
International Search Report Issued for PCT/JP2019/019848, dated Aug. 6, 2019.
Written Opinion of the International Searching Authority issued for PCT/JP2019/019848, dated Aug. 6, 2019.

* cited by examiner

STICKING-TYPE DEEP BODY THERMOMETER

CROSS REFERENCE TO RELATED APPLICATIONS

The present application is a continuation of International application No. PCT/JP2019/019848, filed May 20, 2019, which claims priority to Japanese Patent Application No. 2018-097443, filed May 21, 2018, the entire contents of each of which are incorporated herein by reference.

FIELD OF THE INVENTION

The present invention relates to a sticking-type deep body thermometer that is stuck to a living body to measure a deep body temperature.

BACKGROUND OF THE INVENTION

A thermometer that is stuck to a body surface to acquire body temperature data by continuously measuring a body temperature has been proposed. For example, Patent Document 1 describes a non-heating-type thermometer stuck to a body surface of a subject under test to measure a deep body temperature of the subject under test.

More specifically, the thermometer includes first and second thermal resistors in each of which a first temperature sensor is disposed on one-side surface that contacts with a body surface and a second temperature sensor disposed on the other-side surface opposite from the one-side surface, an equalizing member configured to cover only the other-side surface of each of the first and second thermal resistors, a thermal insulation member disposed to surround a side surface of each of the first and second thermal resistors, and a protection member of which a peripheral portion is fixed to the other-side surface of the thermal insulation member and a center portion is disposed with a predetermined space from the equalizing member. The entire body surface-side of the thermometer is covered with sticking tape (adhesive layer).

Patent Document 1: Japanese Unexamined Patent Application Publication No. 2012-154859

SUMMARY OF THE INVENTION

With the thermometer described in Patent Document 1, the entire body surface side of the thermometer is covered with the sticking tape (adhesive layer), so the thermometer is able to be easily attached to the body surface of a subject under test. However, since the thermometer is stuck to the body surface with sticking tape, the thermometer can be detached from the body surface during measurement. For this reason, there has been a request to detect the attachment and detachment of the thermometer. Particularly, a technique for detecting the attachment and detachment of the thermometer without adding a dedicated component or the like, that is, without increasing cost, has been desired.

The present invention has been made to solve the above-described problem and it is an object of the present invention to provide a sticking-type deep body thermometer that is stuck to a living body to measure a deep body temperature and that is capable of detecting attachment and detachment without adding a new dedicated component, that is, without increasing cost.

A sticking-type deep body thermometer according to the present invention is a sticking-type deep body thermometer that is stuck to a living body to measure a deep body temperature and includes a thermometer body; a sticking member having an adhesion property on a bottom surface of the thermometer body; a first thermal resistor having a predetermined thermal resistance and disposed substantially parallel to the sticking member; a first temperature sensor configured to detect a first temperature at a first surface of the first thermal resistor adjacent to the sticking member; a second temperature sensor configured to detect a second temperature at a second surface of the first thermal resistor opposite the first surface; a deep body temperature detection circuit configured to estimate a deep body temperature based on the first temperature and the second temperature; and an attachment/detachment sensor configured to detect attachment and detachment of the sticking-type deep body thermometer in accordance with a temperature difference between the first temperature and the second temperature and/or a temperature rate of change of the first temperature.

With the sticking-type deep body thermometer according to the present invention, a deep body temperature is estimated in accordance with the first temperature and the second temperature, and attachment and detachment of the sticking-type deep body thermometer are detected based on a temperature difference between the first temperature and the second temperature and/or a temperature rate of change of the first temperature. Here, the first temperature is a temperature at a surface, adjacent to the sticking member, of the first thermal resistor disposed substantially parallel to the sticking member stuck to the bottom surface of the sticking-type deep body thermometer (that is, a living body-side temperature), and the second temperature is a temperature at the surface on the back side of the first thermal resistor (that is, an outside air-side temperature). For this reason, when, for example, a body temperature is higher than an outside air temperature, and when the sticking-type deep body thermometer is stuck to a living body (body surface), the first temperature is higher than the second temperature. When the sticking-type deep body thermometer is attached or detached, the first temperature (body surface-side temperature) is greater in temperature change and higher in temperature rate of change than the second temperature. Thus, by using such the characteristics of the first temperature and the second temperature and the relation between the first temperature and the second temperature, that is, in accordance with a temperature difference between the first temperature and the second temperature and/or a temperature rate of change of the first temperature, it is possible to detect the attachment and detachment (attachment to a living body or detachment from a living body) of the sticking-type deep body thermometer. When a body temperature is lower than an outside air temperature, the high/low (magnitude) relation between the first temperature and the second temperature is inverted; however, it is possible to similarly detect attachment and detachment. As a result, in the sticking-type deep body thermometer that is stuck to a living body to measure a deep body temperature is capable of detecting attachment and detachment without adding a new dedicated component, that is, without increasing cost.

According to the present invention, in the sticking-type deep body thermometer that is stuck to a living body to measure a deep body temperature, it is possible to detect attachment and detachment without adding a new dedicated component, that is, without increasing cost.

DETAILED DESCRIPTION OF THE PREFERRED EMBODIMENTS

Figure 1:
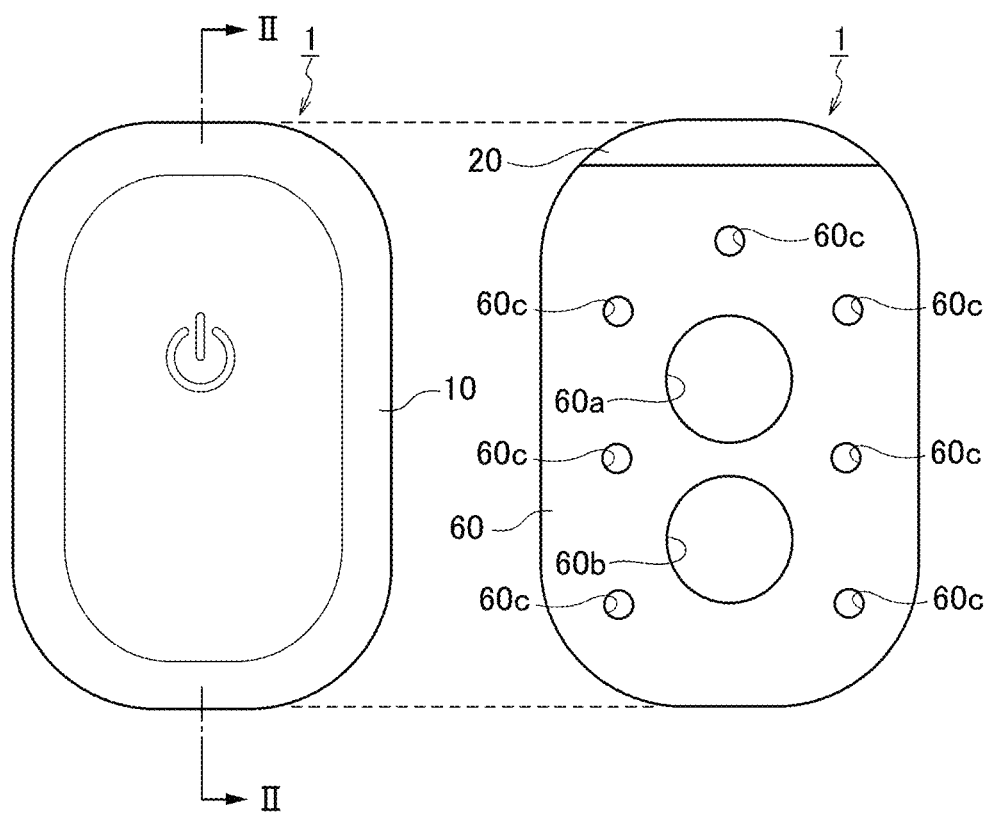
FIG. 1 shows a plan view and a bottom view showing the appearance of a sticking-type deep body thermometer according to an embodiment.

Hereinafter, a preferred embodiment of the present invention will be described in detail with reference to the drawings. In the drawings, like reference signs are assigned to the same or corresponding portions. In the drawings, like reference signs denote the same components, and the description thereof is omitted.

Figure 2:
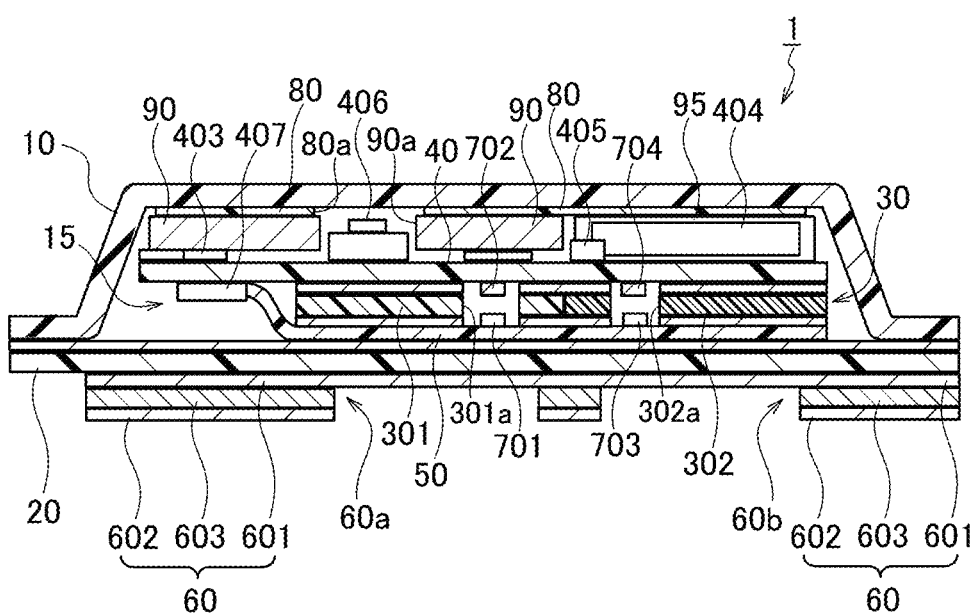
FIG. 2 is a cross-sectional view showing the configuration of the sticking-type deep body thermometer according to the embodiment.
Figure 3:
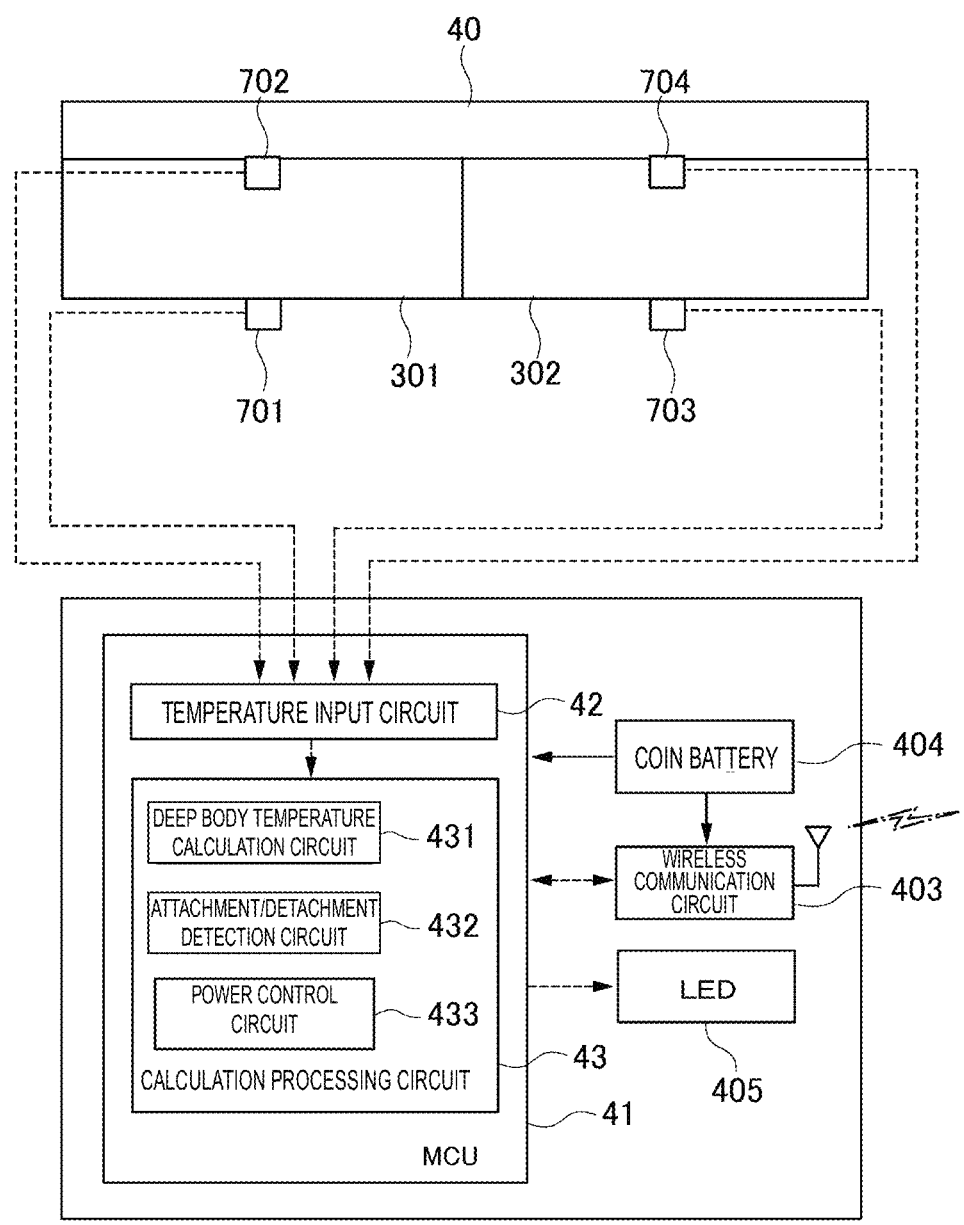
FIG. 3 is a block diagram showing the functional configuration of a processing circuit that is a component of the sticking-type deep body thermometer according to the embodiment.
Figure 4:
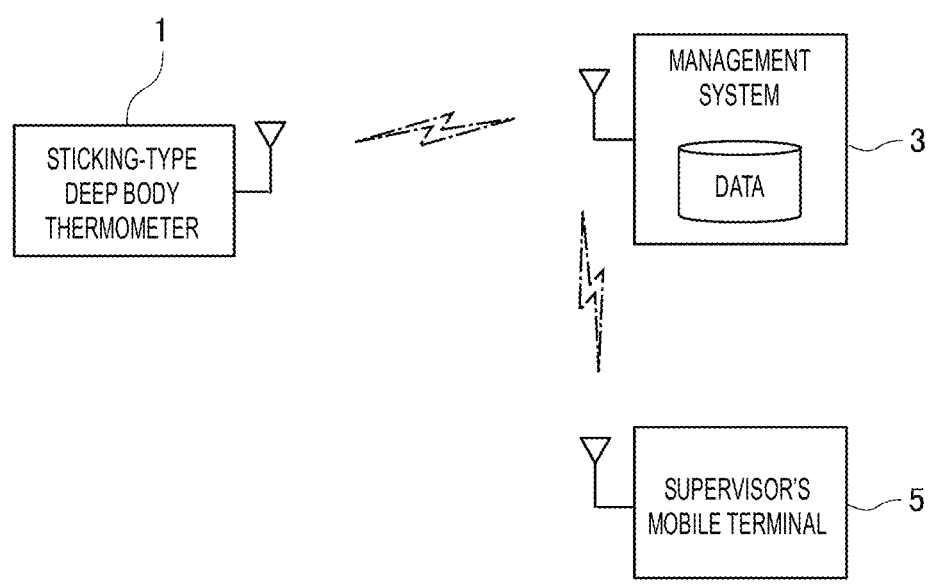
FIG. 4 is a block diagram showing the overall configuration of a deep body temperature measurement system to which the sticking-type deep body thermometer according to the embodiment is applied.

First, the configuration of a sticking-type deep body thermometer (hereinafter, which may be simply referred to as deep body thermometer or thermometer) 1 according to the embodiment will be described with reference to FIG. 1 to FIG. 4. FIG. 1 shows a plan view and a bottom view showing the appearance of the sticking-type deep body thermometer 1. FIG. 2 is a cross-sectional view showing the configuration of the sticking-type deep body thermometer 1 (cross-sectional view taken along the line II-II in FIG. 1). FIG. 3 is a block diagram showing the functional configuration of a processing circuit 41 that is a component of the sticking-type deep body thermometer 1. FIG. 4 is a block diagram showing the overall configuration of a deep body temperature measurement system to which the sticking-type deep body thermometer 1 is applied.

The deep body thermometer 1 is a non-heating-type deep body thermometer that obtains a heat flow from a deep part of a user (subject) to acquire a deep body temperature in accordance with a difference between temperatures respectively detected by a first temperature sensor 701 and a second temperature sensor 702 and a difference between temperatures respectively detected by a third temperature sensor 703 and a fourth temperature sensor 704. The deep body thermometer 1 is a sticking-type (patch-type) deep body thermometer that is stuck to a body surface of a user (subject) to acquire body temperature data by continuously measuring a body temperature.

The deep body thermometer 1 mainly includes an upper exterior body 10, a lower exterior body 20, a body temperature measurement unit 15, a lining member 80, a shock-absorbing member 90, and a sticking member 60. The body temperature measurement unit 15 mainly includes a thermal resistor layer 30, a wiring substrate 40, and a flexible substrate 50. The second temperature sensor 702 and the fourth temperature sensor 704 are mounted on the wiring substrate 40. The first temperature sensor 701 and the third temperature sensor 703 are mounted on the flexible substrate 50.

The upper exterior body 10 is made of, for example, a closed-cell or semi-closed-cell foamed material having waterproof and heat retaining properties. The upper exterior body 10 is preferably made of a foamed material having a low thermal conductivity to prevent a local change in the temperature of the body temperature measurement unit 15 due to a steep variation (change) in outside air temperature. For example, polyurethane, polystyrene, polyolefin, or the like is suitably used as the material. For example, vacuum forming is suitably used as a method of machining the upper exterior body 10. The upper exterior body 10 has a substantially hat shape in cross section so that the body temperature measurement unit 15 (the thermal resistor layer 30, the wiring substrate 40, the flexible substrate 50, and the like) can be accommodated. Therefore, the side surface of the thermal resistor layer 30 is covered with a foamed material, and exposure of the side surface of the thermal resistor layer 30 to outside air is prevented.

The lower exterior body 20 is made from, for example, a non-foamed resin film having a waterproof property (low moisture permeability) and a higher thermal conductivity than the upper exterior body 10. Examples of the material include polypropylene, polyethylene, polyester, and polyimide. Particularly, polyethylene terephthalate (PET) is suitably used as the material. The lower exterior body 20 is formed in a planar shape (flat) so that the flexible substrate 50 on which the first temperature sensor 701 and the third temperature sensor 703 are mounted (the body temperature measurement unit 15) can be fixed in close contact with the lower exterior body 20. When there is a gap between the body temperature measurement unit 15 and the lower exterior body 20, a thermal resistance varies and influences heat flux, so the body temperature measurement unit 15 and the lower exterior body 20 are desirably fixed in close contact with each other by double-faced adhesive tape, adhesive, or the like. The upper exterior body 10 and the lower exterior body 20 are formed to have the same (or substantially the same) sizes (outside dimensions) and are formed to have a size of, for example, about 40 to about 100 (mm) long and about 20 to about 60 (mm) wide.

A peripheral portion of the upper exterior body 10 formed in a substantially hat shape in cross section and a peripheral portion of the lower exterior body 20 formed in a planar shape are, for example, brought into close contact with each other by sticking together with double-faced adhesive tape, fixing by adhesive, heat sealing, or the like. To implement waterproof performance, it is desirable that a portion where the upper exterior body 10 and the lower exterior body 20 are fixed in close contact with each other be flat and less prone to wrinkling. In other words, it is desirable that the outer peripheral portion of the lower exterior body 20 be flat, the outer peripheral portion of the opposed upper exterior body 10 be also flat, and that they be stuck to each other so as to be fixed in close contact with each other. With this configuration, a force uniformly acts on a close contact fixing portion, so inconvenience that adversely influences waterproof performance, such as wrinkling, is less likely to occur.

As shown in FIG. 2, the body temperature measurement unit 15 is made by laminating the flexible substrate 50, the thermal resistor layer 30, and the wiring substrate 40 in this order from the lower exterior body 20 side.

The thermal resistor layer 30 includes two thermal resistors having different thermal resistance values, that is, a first thermal resistor 301 and a second thermal resistor 302, to form two heat fluxes. A material having a higher thermal conductivity (lower thermal resistance value) than the second thermal resistor 302, for example, plastics, such as polypropylene, polyethylene, acrylic, polycarbonate, and epoxy resin, is suitably used as the first thermal resistor 301. A material having a lower thermal conductivity (higher thermal resistance value) than the first thermal resistor 301, for example, foamed plastics (foamed material), such as polyurethane, polystyrene, and polyolefin, is suitably used as the second thermal resistor 302. Non-foamed plastics, rubber, or the like may also be used. Here, the thermal conductivity of a metal, such as copper and aluminum, is higher than or equal to 100 [W/m/K]; whereas the thermal conductivity of plastics, such as polypropylene, polyethylene, acrylic, polycarbonate, and epoxy resin, is about 0.1 to 0.5 [W/m/K] and smaller by about three orders of magnitude. The thermal conductivity of foamed plastics is further smaller by about an order of magnitude. The thermal conductivity of air is further smaller and is 0.024 [W/m/K]. The first thermal resistor 301 and the second thermal resistor 302 are formed to have substantially the same thickness in order to reduce cost by enabling the first thermal resistor 301 and the second thermal resistor 302 to be stacked with the wiring substrate 40 and the flexible substrate 50.

The first thermal resistor 301 that is a component of the thermal resistor layer 30 has a first through-hole 301a extending through in a thickness direction. Similarly, the second thermal resistor 302 that is a component of the thermal resistor layer 30 has a second through-hole 302a extending through in a thickness direction. When the first through-hole 301a is viewed in plan, the first through-hole 301a is formed such that the first temperature sensor 701 and the second temperature sensor 702 are accommodated inside. In other words, the pair of first temperature sensor 701 and second temperature sensor 702 is disposed along the thickness direction of the first thermal resistor 301 within (inside) the first through-hole 301a. Similarly, when the second through-hole 302a is viewed in plan, the second through-hole 302a is formed such that the third temperature sensor 703 and the fourth temperature sensor 704 are accommodated inside. In other words, the pair of third temperature sensor 703 and fourth temperature sensor 704 is disposed along the thickness direction of the second thermal resistor 302 within (inside) the second through-hole 302a.

For example, a thermistor, a resistance thermometer sensor, or the like is suitably used as each of the first temperature sensor 701 to the fourth temperature sensor 704 (hereinafter, which may be collectively referred to as temperature sensors 70). Each temperature sensor 70 desirably has a thermal capacity as small as possible from the viewpoint of enhancing response. Thus, for example, a chip thermistor is suitably used as each temperature sensor 70. Each of the first temperature sensor 701 to the fourth temperature sensor 704 is electrically connected to the processing circuit 41 (described later) via a printed circuit, and the processing circuit 41 reads an electrical signal (voltage value) corresponding to a temperature.

Incidentally, to reduce the size of the heat flow deep body thermometer 1, it is important to reduce the size of the thermal resistor layer 30 (the first thermal resistor 301 and the second thermal resistor 302); however, when the size of the thermal resistor layer 30 is reduced, a difference between the output values of the paired temperature sensors 70 reduces, so there are concerns that a measurement error increases. Here, each temperature sensor 70 (i.e., a chip thermistor) has a substantially rectangular parallelepiped shape and has a thickness, so the thickness cannot be ignored when the thermal resistor layer 30 becomes thinner. When the temperature sensor 70 is in contact with the side surface of the thermal resistor layer 30, heat is transferred from the contact portion, so there are concerns that the temperature (detected value) of the temperature sensor 70 becomes a temperature (value) that deviates from the surface temperature of the thermal resistor layer 30. Therefore, to reduce the influence thereof, the through-holes 301a, 302a are formed in the thermal resistor layer 30 around the temperature sensors 70 to provide such a structure that the temperature sensors 70 are not in contact with the side surface of the thermal resistor layer 30.

The wiring substrate 40 is, for example, a rigid substrate like a glass epoxy substrate. The processing circuit 41 is implemented on or in the wiring substrate 40. The processing circuit 41 acquires deep body temperature data by processing output signals of the first temperature sensor 701 to the fourth temperature sensor 704. A wireless communication circuit 403 and a coin battery 404 are mounted on the wiring substrate 40. The wireless communication circuit 403 transmits (outputs) acquired deep body temperature data. The coin battery 404 supplies electric power to the processing circuit 41 and the wireless communication circuit 403. The processing circuit 41 mainly includes a temperature input circuit 42 and a calculation processing circuit 43. The temperature input circuit 42 is configured to include, for example, an amplifier (for example, an operational amplifier), an analog/digital converter (A/D converter), and the like to read detection signals (output voltages) of the temperature sensors 70. The temperature input circuit 42 amplifies an analog signal output from each temperature sensor 70, converts the analog signal to a digital signal, and outputs the digital signal to the calculation processing circuit 43.

The calculation processing circuit 43 is made up of, for example, an MCU (micro control unit), EEPROM, RAM, and the like. The calculation processing circuit 43 calculates a deep body temperature from the read temperature data and detects the attachment and detachment of the deep body thermometer 1. The details will be described later.

The second temperature sensor 702 and the fourth temperature sensor 704 are mounted on the bottom surface of the wiring substrate 40. The second temperature sensor 702 acquires the temperature of the top surface (outside air side) of the first thermal resistor 301. The fourth temperature sensor 704 detects the temperature of the top surface (outside air side) of the second thermal resistor 302. More specifically, a pair of heat equalizing patterns that equalize a surrounding temperature distribution is formed on the bottom surface of the wiring substrate 40, one of electrodes of the second temperature sensor 702 is connected to one of the heat equalizing patterns, and one of electrodes of the fourth temperature sensor 704 is connected to the other one of the heat equalizing patterns. The pair of heat equalizing patterns is made of, for example, a material having a high thermal conductivity, such as a metal film.

To prevent a change in only the temperature of part of the wiring substrate 40 due to the influence of outside air temperature or the like, it is desirable that an equalizing member (i.e., a metal film) that has a high thermal conductivity and that thermally equalizes the influence of a temperature distribution of outside air temperature be provided on the back surface side (outside air side) of a wiring layer on which the second temperature sensor 702 and the fourth temperature sensor 704 are mounted. A metal foil, a metal thin sheet, or the like may be used as the equalizing member, and, as in the case of the wiring layer formed on or in the wiring substrate 40, it is desirable that the equalizing member be formed as a wiring pattern (solid pattern) of an inner layer of the wiring substrate 40 (multilayer rigid substrate). In this case, the wiring pattern of the inner layer, used as the equalizing member, may be a ground pattern, and it is desirable that the wiring pattern be an independent pattern not connected to the electrical circuit and through which no current flows.

The wireless communication circuit 403 transmits acquired deep body temperature data (living body information), attachment/detachment information indicating that the deep body thermometer 1 is attached or detached, and the like to an external management device and management system 3 (for example, a server or the like) (see FIG. 4). Here, the wireless communication circuit 403 transmits deep body temperature data to the external management device and management system 3 by using, for example, Bluetooth (registered trademark) or the like. When the management device and management system 3 receives attachment/detachment information, the management device and management system 3 desirably transmits (transfers) the attachment/detachment information to a mobile terminal 5 (for example, a smartphone or the like) of a manager or supervisor (for example, a nurse, a field supervisor, or the like). Thus, it is possible to make a manager or a supervisor recognize an attachment/detachment state of the detachable deep body thermometer 1. Alternatively, the wireless communication circuit 403 may be configured to directly transmit the attachment/detachment information to the mobile terminal 5 of a manager or supervisor. On the other hand, the wireless communication circuit 403 may receive, for example, outside air temperature data or the like from the external management device and management system 3 or the mobile terminal 5.

The low-profile coin battery (battery) 404 supplies electric power to the above-described processing circuit 41, wireless communication circuit 403, and the like. The coin battery 404 is accommodated in a battery holder 95 mounted on (attached to) the wiring substrate 40. The battery holder 95 is disposed between the wiring substrate 40 and the lining member 80. In other words, the battery holder 95 also serves as a spacer member that supports the lining member 80. To reduce the plane area (sticking area) of the body temperature measurement unit 15 (deep body thermometer 1), and also to prevent the influence of heat generation resulting from a change in outside air temperature or the operation of the wireless communication circuit 403, the wireless communication circuit 403 and the coin battery 404 (battery holder 95) are disposed across the wiring substrate 40 from the temperature sensors 70 (top surface side).

A power switch 406 is mounted on the top surface (main surface) of the wiring substrate 40. The power switch 406 receives user's on/off operation of the power via the upper exterior body 10. The wiring substrate 40 is accommodated in an enclosed space defined by the upper exterior body 10 and the lower exterior body 20 such that the power switch 406 faces the rear surface (back surface) of the upper exterior body 10. For example, a push button switch, a rocker switch, or the like is suitably used as the power switch 406. In the case of a push button switch, it is desirable that the push button switch be of an alternate action type that retains an on state even when a fingertip is released. A surface mount-type switch is desirable as the power switch 406; however, a reed-type switch may also be used.

To prevent erroneous (accidental) pushing down of the power switch 406 to turn on or off the power, and also to make the power switch 406 not push up the upper exterior body 10, the power switch 406 is disposed so as not to be in contact with the upper exterior body 10. More specifically, a clearance between the button top surface (top surface) of the power switch 406 and the rear surface (back surface) of the upper exterior body 10 is, for example, desirably set within a range of 0 to 4 (mm) and more desirably set within a range of 0.5 to 1.5 (mm). The stroke of the power switch 406 is, for example, desirably set within a range of 0.1 to 1 (mm) and more desirably set within a range of 0.1 to 0.3 (mm).

An LED 405 is mounted on the top surface of the wiring substrate 40. The LED 405 lights up or blinks in accordance with user's operation or the status of measurement of deep body temperature (for example, an on/off state of the power switch 406, measurement start/stop, attachment/detachment state, and the like). For example, a VCSEL or the like may be used instead of the LED. In addition, an FPC connector 407 for electrically connecting the flexible substrate 50 is attached to the bottom surface side of the wiring substrate 40.

The flexible substrate (FPC) 50 is made of, for example, polyimide, polyester (PET), or the like and has flexibility. The first temperature sensor 701 and the third temperature sensor 703 are mounted on the flexible substrate 50. The first temperature sensor 701 acquires the skin-side temperature of the first thermal resistor 301. The third temperature sensor 703 acquires the skin-side temperature of the second thermal resistor 302. More specifically, a pair of heat equalizing patterns is formed on the flexible substrate 50 to equalize the surrounding temperature distribution, one of terminals of the first temperature sensor 701 is connected to one of the heat equalizing patterns, and one of terminals of the third temperature sensor 703 is connected to the other one of the heat equalizing patterns. The pair of heat equalizing patterns is made of, for example, a material having a high thermal conductivity, such as a metal film. Each of the first temperature sensor 701 and the third temperature sensor 703 is connected to the wiring substrate 40 (processing circuit 41) via the wiring pattern and the above-described FPC connector 407. The processing circuit 41 (temperature input circuit 42) reads an electrical signal (voltage value) corresponding to a temperature. As described above, the lower exterior body 20, the flexible substrate 50, the thermal resistor layer 30, and the wiring substrate 40 form heat fluxes, so these components are, for example, fixed in close contact with each other by double-faced adhesive tape such that no gap is formed therebetween.

The lining member 80 is disposed between the rear surface (back surface) of the upper exterior body 10, that is, the upper exterior body 10, and both the shock-absorbing member 90 and the battery holder (spacer member) 95. The lining member 80 is formed in a thin sheet shape thinner than the shock-absorbing member 90 (described later). The lining member 80 is installed such that, in order to reduce wrinkling of the upper exterior body 10, one of the surfaces is stuck to the rear surface (back surface) of the upper exterior body 10 by, for example, double-faced adhesive tape or the like. The lining member 80 is, for example, made of a resin material, such as PET, having flexibility so as to be flexible (bendable) in an operation direction (for example, push-down direction) of the power switch 406. The lining member 80 may be made from a thin metal sheet or the like.

The lining member 80 has a through-hole 80a in the thickness direction. The power switch 406 fits inside the through-hole 80a when the lining member 80 is viewed in plan. The through-hole 80a may be formed such that the circumference of the hole is completely closed or may be formed such that the circumference of the hole is not completely closed. The through-hole 80a of the lining member 80 is formed to such a size that is smaller than the outside diameter of a fingertip to avoid entry of the entire fingertip and that allows a ball of a fingertip to enter to push the power switch 406. More specifically, since there are variations in the outside diameter of a fingertip among individuals, the inside diameter of the through-hole 80a is, for example, desirably set within a range of 10 to 20 (mm) and more desirably set within a range of 13 to 16 (mm). When the thickness of the upper exterior body 10 is thick (when, the thickness is greater than or equal to, for example, 2 (mm)), it is desirable to increase the inside diameter of the through-hole 80a in accordance with the thickness of the upper exterior body 10.

The shock-absorbing member 90 having shock-absorbing characteristics (cushioning characteristics) and formed in a sheet shape is disposed between the top surface (main surface) of the wiring substrate 40 and the lining member 80. The shock-absorbing member 90 is formed so as to be thicker than a level (height) from the mounting surface of the wiring substrate 40 for the power switch 406 mounted on the wiring substrate 40 and a level (height) from the mounting surface of the wiring substrate 40 for electronic components. The shock-absorbing member 90 is installed by being stuck to the other surface of the lining member 80 by using, for example, double-faced adhesive tape or the like.

The shock-absorbing member 90 has a through-hole 90a in the thickness direction. The power switch 406 fits inside the through-hole 90a when the shock-absorbing member 90 is viewed in plan. The through-hole (opening portion) 90a formed in the shock-absorbing member 90 is formed and disposed so as to fit inside the through-hole (opening portion) 80a formed in the lining member 80 when viewed in plan. In other words, the through-hole 90a of the shock-absorbing member 90 is formed so as to be smaller than the through-hole 80a of the lining member 80. Each of the through-hole 90a formed in the shock-absorbing member 90 and the through-hole 80a formed in the lining member 80 has a substantially circular shape (including, for example, an elliptical shape or the like) and is set (formed) such that the inside diameter is smaller than the outside diameter of a fingertip. More specifically, the inside diameter of the through-hole 90a of the shock-absorbing member 90 is, for example, desirably set within a range of 8 to 18 (mm) and more desirably set within a range of 11 to 14 (mm). When the upper exterior body 10 is thick (for example, thicker than or equal to 2 (mm)), it is desirable that the inside diameter of the through-hole 90a be increased in accordance with the thickness.

The sticking member 60 includes a first adhesion layer 601, a vent layer 603, and a second adhesion layer 602. The first adhesion layer 601 is stuck to an outer-side surface of the lower exterior body 20. The vent layer 603 has air permeability (that is, a moisture permeable layer that allows passage of moisture) and is stuck to the first adhesion layer 601. The second adhesion layer 602 is stuck to the vent layer 603. Incidentally, when the deep body thermometer 1 is stuck to a skin and is used, skin irritation may be caused if sweat remains accumulated for a long period of time between the skin and the deep body thermometer 1 (lower exterior body 20); however, stuffiness due to sweat or the like is reduced by providing the sticking member 60 with the vent layer 603 that allows passage of moisture. For example, nonwoven fabric may be suitably used as the vent layer 603 (moisture permeable layer). Instead of nonwoven fabric, woven fabric or knitted fabric may be used. Alternatively, paper, wood, sponge/open cell foamed material, or the like may be used, or a plastic, rubber, or metal structure having a groove or hole extending from the center of the body temperature measurement unit 15 toward the periphery may be used.

The vent layer 603 contains air inside, so the vent layer 603 usually has a low thermal conductivity. Therefore, when the vent layer 603 is provided between a skin and the deep body thermometer 1, body temperature measurement accuracy is influenced. Therefore (to stably measure a body temperature), the vent layer 603 is not disposed in a region that overlaps the first temperature sensor 701 and the third temperature sensor 703 that measure the temperature of a skin, and the heat equalizing pattern connected to them.

Here, description will be made by way of an example in which nonwoven fabric is used as the vent layer 603. Two pieces of biocompatible double-faced adhesive tape (the first adhesion layer 601 and the second adhesion layer 602) are respectively stuck to both surfaces of the nonwoven fabric (vent layer 603). Through-holes 60a, 60b are respectively formed in the vent layer 603 and the second adhesion layer 602 in the thickness direction. The first temperature sensor 701 and the third temperature sensor 703 respectively fit within the through-holes 60a, 60b when viewed in plan. Here, it is desirable that no through-hole is formed in the double-faced adhesive tape (first adhesion layer 601) stuck to the lower exterior body 20. This is because, when a through-hole is formed (that is, when no first adhesion layer 601 is provided), there are concerns that the lower exterior body 20 does not closely contact with a skin and, as a result, measurement accuracy decreases.

Ordinarily, the double-faced adhesive tape (second adhesion layer 602) has a lower moisture permeability than the nonwoven fabric (vent layer 603), so it is desirable that a plurality of through-holes 60c formed in the thickness direction be formed in at least the second adhesion layer 602. In this case, it is desirable that, for example, the through-holes 60c having a diameter of about 1 to 10 mm be disposed at intervals of about 2 to 20 mm.

As described above, the calculation processing circuit 43 is made up of, for example, an MCU (micro control unit), EEPROM, RAM, and the like. The calculation processing circuit 43 calculates a deep body temperature and detects the attachment and detachment of the deep body thermometer 1 in accordance with detected values (temperature data) of the temperature sensors 70, read via the temperature input circuit 42 (temperature input circuit). The calculation processing circuit 43 causes memory, such as the RAM, to store the calculated deep body temperature data, the attachment/detachment information, and the like. In addition, the calculation processing circuit 43 wirelessly outputs (transmits) the calculated deep body temperature data, the attachment/detachment information, and the like to the external management device and management system 3 by outputting the calculated deep body temperature data, the attachment/detachment information, and the like, to the wireless communication circuit 403.

Particularly, the calculation processing circuit 43 has a function to detect the attachment and detachment of the deep body thermometer 1 without adding a new dedicated component (for example, another sensor or the like), that is, without increasing cost. Therefore, the calculation processing circuit 43 functionally includes a deep body temperature calculation circuit 431, an attachment/detachment detection circuit 432, and a power control circuit 433. In the calculation processing circuit 43, the functions of the deep body temperature calculation circuit 431, attachment/detachment detection circuit 432, and power control circuit 433 are implemented by the MCU running programs stored in the EEPROM or the like.

The deep body temperature calculation circuit 431 calculates (estimates) a deep body temperature based on a temperature difference between the front and rear of each of the thermal resistors 301, 302, caused by a difference between two heat fluxes formed by using the thermal resistors 301, 302 having two different thermal resistances. More specifically, the deep body temperature calculation circuit 431 calculates a deep body temperature Tb in accordance with, for example, the following expression (1).

$$Tb = \{T1(T3-T4)*Ra1 - T3(T1-T2)*Ra2\}/\{(T3-T4)*Ra1 - (T1-T2)*Ra2\} \quad (1)$$

Tb denotes a deep body temperature, T1 denotes a first temperature detected by the first temperature sensor 701, T2 denotes a second temperature detected by the second temperature sensor 702, and Ra1 denotes a thermal resistance value of the first thermal resistor 301. In addition, T3 denotes a third temperature detected by the third temperature sensor 703, T4 denotes a fourth temperature detected by the fourth temperature sensor 704, and Ra2 denotes a thermal resistance value of the second thermal resistor 302.

Because Ra1 and Ra2 are known, the deep body temperature Tb is uniquely obtained by detecting the four temperatures (T1, T2, T3, T4).

Incidentally, when, for example, a body temperature is higher than an outside air temperature, the body surface side is higher in temperature while the deep body thermometer 1 is stuck to a living body (body surface), so T1>T2, and T3>T4. In addition, the heat of the living body is easy to be released when the thermal resistance is higher, so T3>T1. In other words, T3>T1>T2≈T4. Furthermore, when the deep body thermometer 1 is attached or detached, T1 and T3 (body surface-side temperatures) are higher in temperature rate of change and greater in temperature change than T2 and T4. Therefore, the attachment/detachment detection circuit 432 detects the attachment and detachment of the deep body thermometer 1 (attachment to a living body or detachment from the living body) by using the characteristics of such T1, T2, T3, and T4, the relation between T1 and T2, the relation between T3 and T4, and the relation between T1 and T3. In other words, the attachment/detachment detection circuit 432 detects the attachment and detachment of the deep body thermometer 1 in accordance with at least any one of a temperature difference (T1−T2) between the first temperature T1 and the second temperature T2, a temperature difference (T3−T4) between the third temperature T3 and the fourth temperature T4, a temperature difference (T3−T1) between the third temperature T3 and the first temperature T1, a temperature rate of change ($\Delta T1$) of the first temperature T1, and a temperature rate of change ($\Delta T3$) of the third temperature T3. Detachment and attachment may be detected by using some of these in combination.

More specifically, the attachment/detachment detection circuit 432 determines that attachment or detachment of the deep body thermometer 1 has occurred when, within a predetermined time (within, for example, 20 seconds), the sign of the temperature difference (T1−T2) between the first temperature T1 and the second temperature T2 is inverted and the absolute value (|T1−T2|) of the temperature difference becomes greater than or equal to a predetermined threshold value (which corresponds to a fifth threshold value). Instead of or in addition to the temperature difference (T1−T2) between the first temperature T1 and the second temperature T2, the attachment/detachment detection circuit 432 may determine that attachment or detachment of the deep body thermometer 1 has occurred when, within a predetermined time (within, for example, 20 seconds), the sign of the temperature difference (T3−T4) between the third temperature T3 and the fourth temperature T4 is inverted and the absolute value (|T3−T4|) of the temperature difference becomes greater than or equal to a predetermined threshold value (which corresponds to a sixth threshold value).

Figure 5:
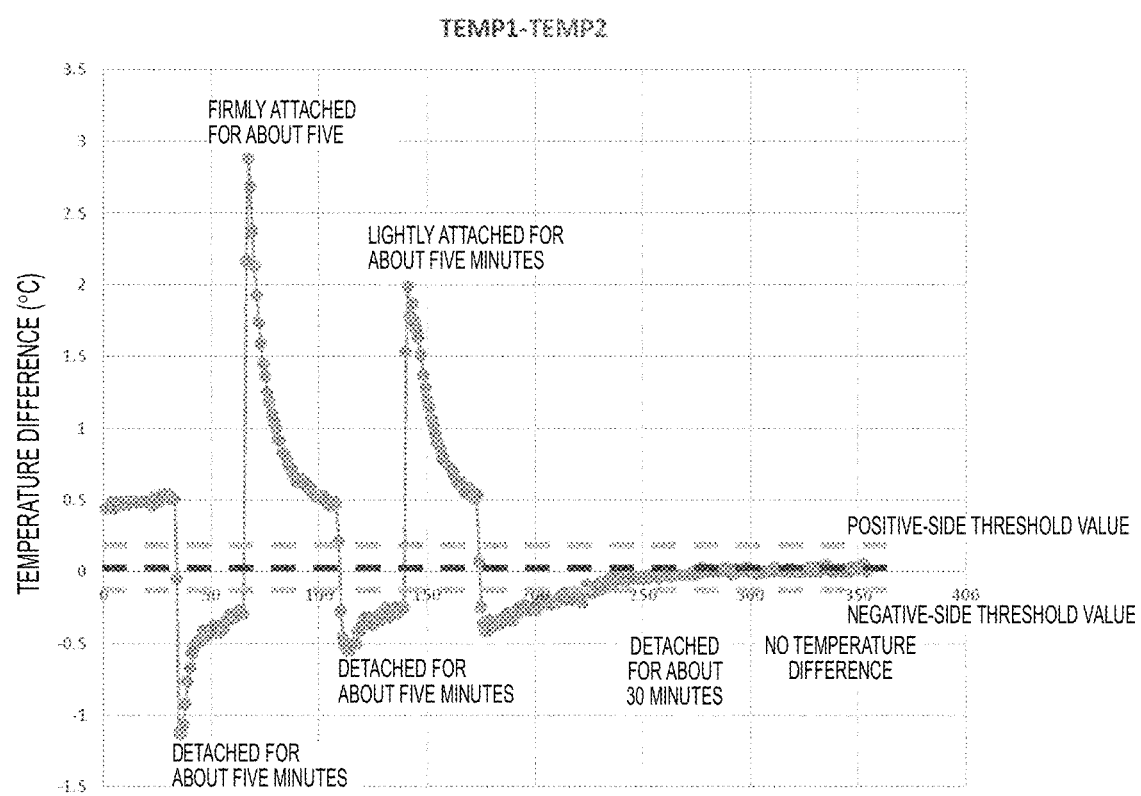
FIG. 5 is a graph showing an example of changes in temperature difference between a first temperature and a second temperature, resulting from attachment and detachment of the sticking-type deep body thermometer.

Here, FIG. 5 shows an example of changes in the temperature difference (T1−T2) between the first temperature T1 and the second temperature T2, resulting from attachment and detachment of the deep body thermometer 1. In FIG. 5, the abscissa axis represents data point number (that is, time), and the ordinate axis represents temperature difference (° C.). A sampling period is 10 (sec). When a body temperature is higher than an outside air temperature, T1−T2 (temperature difference) decreases over a minus (negative)-side threshold value when the deep body thermometer 1 is detached as shown in FIG. 5. On the other hand, when the deep body thermometer 1 is attached, T1−T2 (temperature difference) increases over a plus (positive)-side threshold value. Therefore, when T1−T2 exceeds the plus (positive)-side threshold value, it may be determined that the deep body thermometer 1 is attached (mounted). On the other hand, when T1−T2 exceeds the minus (negative)-side threshold value, it may be determined that the deep body thermometer 1 is detached. When a body temperature is lower than an outside air temperature, the magnitude (high/low) relation between the first temperature T1 and the second temperature T2 is inverted.

Similarly, the attachment/detachment detection circuit 432 may determine that attachment or detachment of the deep body thermometer 1 has occurred when, within a predetermined time (within, for example, 20 seconds), the sign of the temperature difference (T3−T1) between the third temperature T3 and the first temperature T1 is inverted and the absolute value (|T3−T1|) of the temperature difference becomes greater than or equal to a predetermined threshold value (which corresponds to a fourth threshold value).

Figure 8:
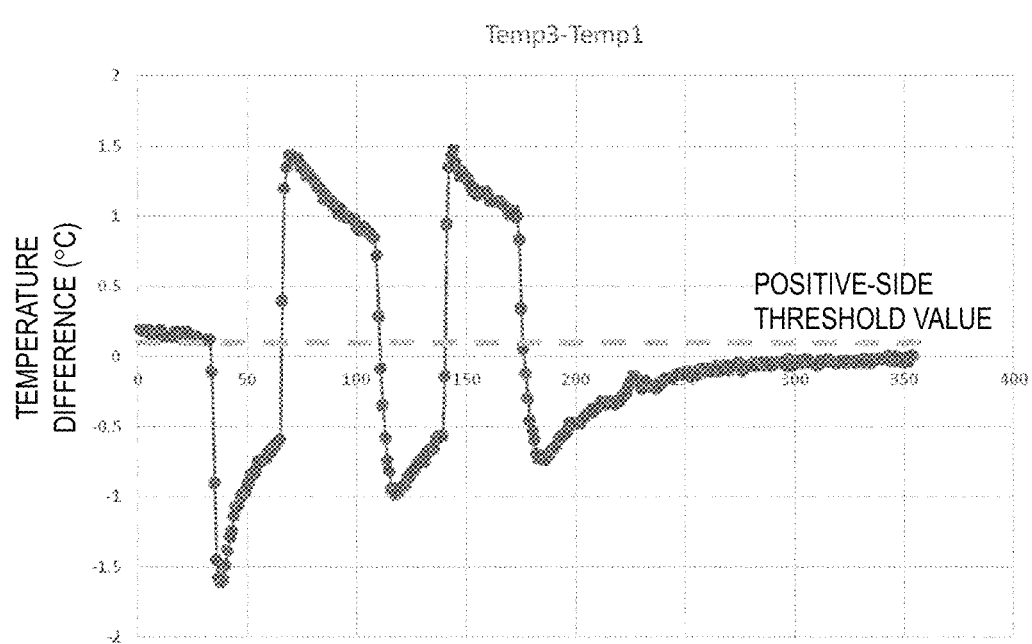
FIG. 8 is a graph showing an example of changes in temperature difference between a third temperature and a first temperature, resulting from attachment and detachment of the sticking-type deep body thermometer.

Here, FIG. 8 shows an example of changes in the temperature difference (T3−T1) between the third temperature T3 and the first temperature T1, resulting from attachment and detachment of the deep body thermometer 1. In FIG. 8, the abscissa axis represents data point number (that is, time), and the ordinate axis represents temperature difference (° C.). A sampling period is 10 (sec). When a body temperature is higher than an outside air temperature, T3−T1 (temperature difference) decreases over a minus (negative)-side threshold value when the deep body thermometer 1 is detached as shown in FIG. 8. On the other hand, when the deep body thermometer 1 is attached, T3−T1 (temperature difference) increases over a plus (positive)-side threshold value. Therefore, when T3−T1 exceeds the plus (positive)-side threshold value, it may be determined that the deep body thermometer 1 is attached (mounted). On the other hand, when T3−T1 exceeds the minus (negative)-side threshold value, it may be determined that the deep body thermometer 1 is detached. When a body temperature is (high/low) relation between the third temperature T3 and the first temperature T1 is inverted.

The attachment/detachment detection circuit 432 is also capable of determining that attachment or detachment of the deep body thermometer 1 has occurred when the absolute value of the temperature rate of change (ΔT3) of the third temperature T3 becomes greater than or equal to a predetermined threshold value (which corresponds to a seventh threshold value). Similarly, the attachment/detachment detection circuit 432 is also capable of determining that attachment or detachment of the deep body thermometer 1 has occurred when the absolute value of the temperature rate of change (ΔT1) of the first temperature T1 becomes greater than or equal to a predetermined threshold value (which corresponds to a second threshold value).

Figure 6:
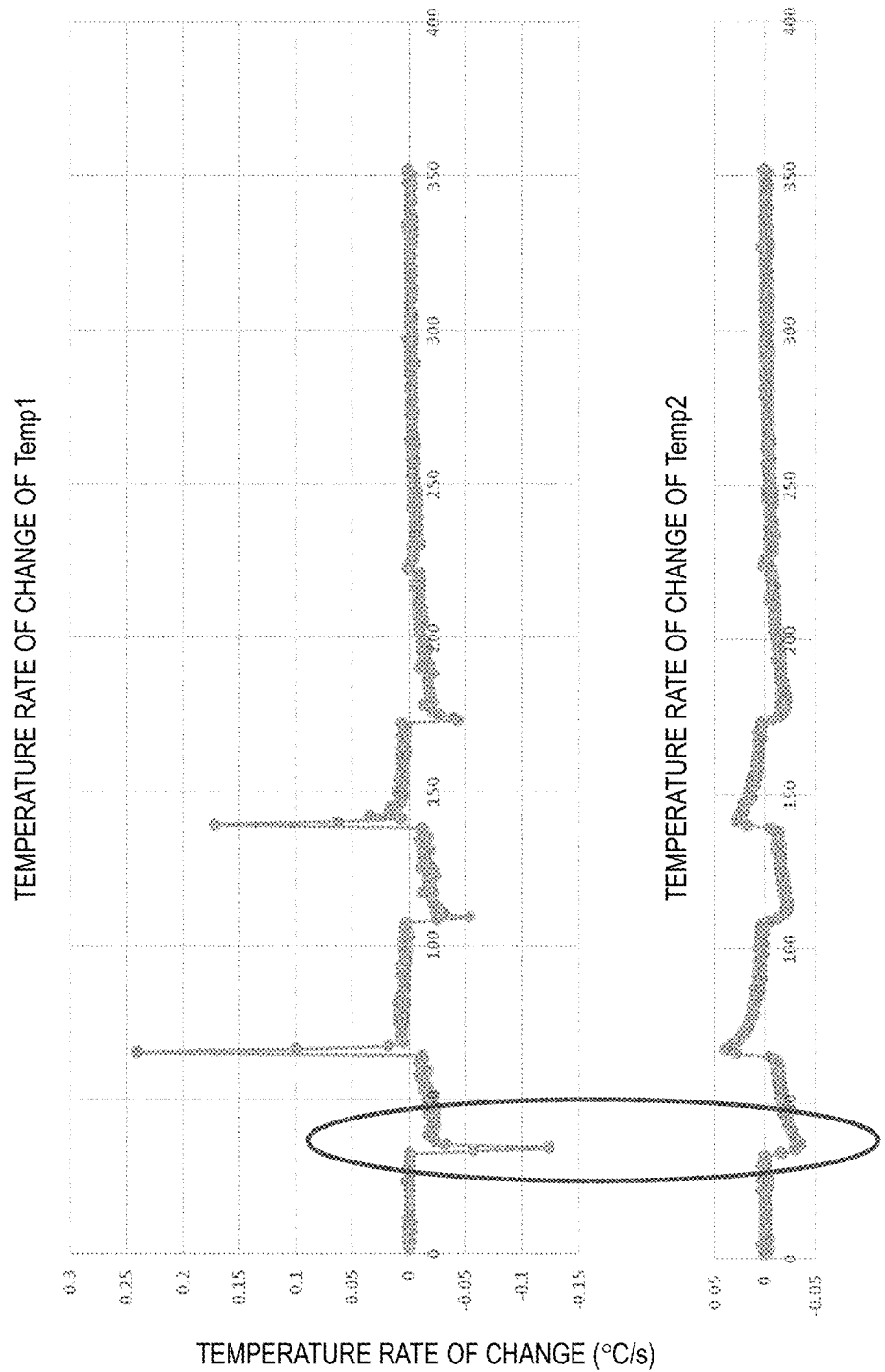
FIG. 6 is a graph showing an example of changes in temperature rate of change of the first temperature and changes in temperature rate of change of the second temperature, resulting from attachment and detachment of the sticking-type deep body thermometer.
Figure 7:
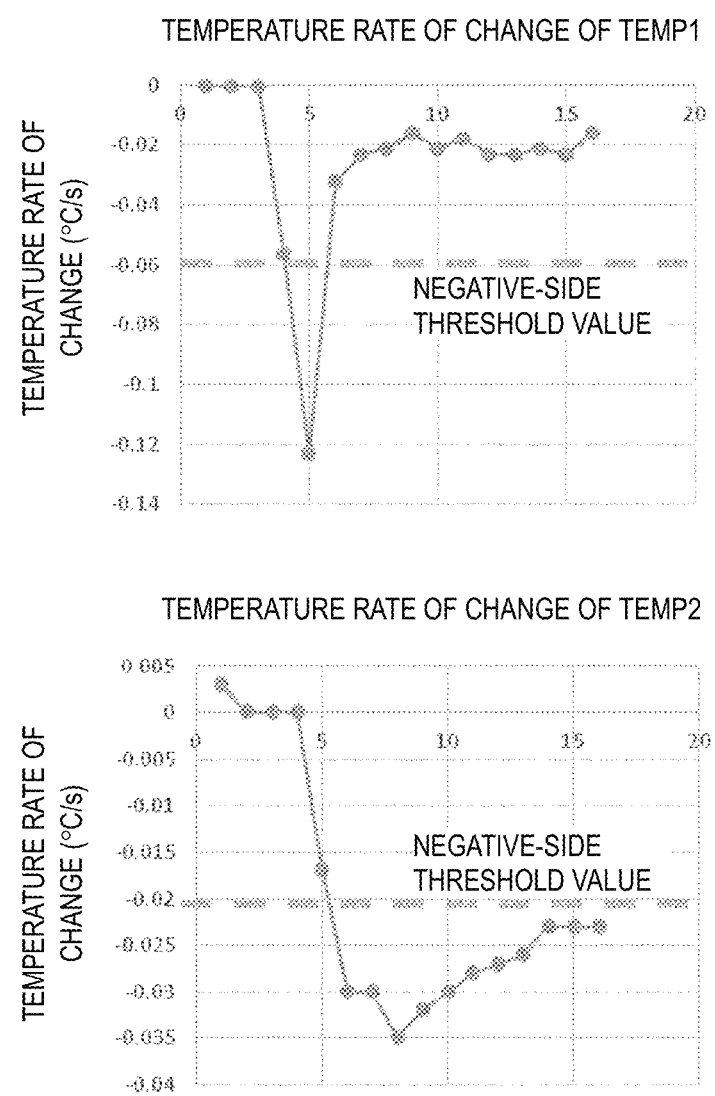
FIG. 7 is an enlarged graph of part (relevant part) of FIG. 6.

Here, the top graph of FIG. 6 shows an example of changes in the temperature rate of change (ΔT1) of the first temperature T1, resulting from attachment and detachment of the deep body thermometer 1. The top graph of FIG. 7 shows an enlarged view of a portion marked by the ellipse (relevant portion) in FIG. 6. In FIG. 6 and FIG. 7, the abscissa axis represents data point number (that is, time), and the ordinate axis represents temperature rate of change (° C./sec). A sampling period is 10 (sec). When a body temperature is higher than an outside air temperature, ΔT1 (temperature rate of change) decreases over a minus (negative)-side threshold value when the deep body thermometer 1 is detached as shown in the top graphs of FIG. 6 and FIG. 7. On the other hand, when the deep body thermometer 1 is attached, ΔT1 (temperature rate of change) increases over a plus (positive)-side threshold value. Therefore, when ΔT1 exceeds the plus (positive)-side threshold value, it may be determined that the deep body thermometer 1 is attached (mounted). On the other hand, when ΔT1 (ΔT2) exceeds the minus (negative)-side threshold value, it may be determined that the deep body thermometer 1 is detached. When a body temperature is lower than an outside air temperature, the signs of ΔT1 and ΔT3 are inverted.

Furthermore, the attachment/detachment detection circuit 432 desirably determines that attachment or detachment of the deep body thermometer 1 has occurred when the absolute value of the temperature rate of change (ΔT3) of the third temperature T3 becomes greater than or equal to a predetermined threshold value (which corresponds to a seventh threshold value) and the absolute value of the temperature rate of change (ΔT4) of the fourth temperature T4 becomes greater than or equal to a predetermined threshold value (which corresponds to an eighth threshold value). Similarly, the attachment/detachment detection circuit 432 desirably determines that attachment or detachment of the deep body thermometer 1 has occurred when the absolute value of the temperature rate of change (ΔT1) of the first temperature T1 becomes greater than or equal to a predetermined threshold value (which corresponds to a second threshold value) and the absolute value of the temperature rate of change (ΔT2) of the second temperature T2 becomes greater than or equal to a predetermined threshold value (which corresponds to a third threshold value). It is desirable that the seventh threshold value, the eighth threshold value, the second threshold value, and the third threshold value be set such that the seventh threshold value is greater than the eighth threshold value and the second threshold value is greater than the third threshold value.

FIG. 6 shows an example of changes in the temperature rate of change (ΔT1) of the first temperature T1 and the temperature rate of change (ΔT2) of the second temperature T2, resulting from attachment and detachment of the deep body thermometer 1. FIG. 7 shows an enlarged view of a portion marked by the ellipse (relevant portion) in FIG. 6. In FIG. 6 and FIG. 7, the abscissa axis represents data point number (that is, time), and the ordinate axis represents temperature rate of change (° C./sec). A sampling period is 10 (sec). When a body temperature is higher than an outside air temperature, ΔT1 and ΔT2 (temperature rates of change) each decrease over a minus (negative)-side threshold value when the deep body thermometer 1 is detached as shown in FIG. 6 and FIG. 7. On the other hand, when the deep body thermometer 1 is attached, ΔT1 and ΔT2 (temperature rates of change) each increase over a plus (positive)-side threshold value. Because ΔT2 is lower in response than ΔT1, attachment and detachment in a short period of time (attachment and detachment in about, for example, several seconds) are ignored (excluded) by using ΔT2, so it is possible to further reliably detect the attachment and detachment of the deep body thermometer 1.

Incidentally, the attachment/detachment detection circuit 432 assumes (estimates) that the deep body thermometer 1 is attached to the living body and starts attachment/detachment detection when a predetermined time (for example, 10 minutes) has elapsed after the power is turned on or after a measurement is started. Then, the attachment/detachment detection circuit 432 thereafter (subsequently) determines that the deep body thermometer 1 is detached (demounted) when the attachment/detachment detection circuit 432 determines that attachment or detachment of the deep body thermometer 1 has occurred. This is because the result of mounting (attachment) or demounting (detachment) is opposite depending on whether an outside air temperature is higher or lower than a body temperature and, therefore, another mounting or demounting determination is needed; however, there is a possibility of non-mounted state just after power on or just after measurement start, so there are concerns about erroneous detection when attachment/detachment detection is performed in accordance with only the fact that the power is turned on or in accordance with only the fact that a measurement is started.

By using such characteristics that, when left standing for a long period of time in a demounted state, the temperature difference (T3−T1) between the third temperature T3 and the first temperature T1, the temperature difference (T3−T4) between the third temperature T3 and the fourth temperature T4, and the temperature difference (T1−T2) between the first temperature T1 and the second temperature T2 becomes substantially zero, the attachment/detachment detection circuit 432 determines that the deep body thermometer 1 is attached when the temperature difference between T3 and T1, the temperature difference between T3 and T4 and/or the temperature difference between T1 and T2 has exceeded a predetermined threshold value for a predetermined time (for example, 10 minutes).

Body temperature data (deep body temperature Tb) acquired by the deep body temperature calculation circuit 431, attachment/detachment information detected by the attachment/detachment detection circuit 432, and the like are output to the wireless communication circuit 403 and the like. As described above, the wireless communication circuit 403 transmits attachment/detachment information, indicating that the deep body thermometer 1 is attached or detached, to the external management device and management system 3 when attachment or detachment of the deep body thermometer 1 is detected. The wireless communication circuit 403 provides attachment/detachment information to the supervisor's mobile terminal 5 via the management device and management system 3 when attachment or detachment of the deep body thermometer 1 is detected.

The power control circuit 433 shifts the deep body thermometer 1 into a low power consumption mode (sleep mode) or turns off the power of the deep body thermometer 1 when it is determined that the deep body thermometer 1 is detached from the living body.

Modification

Figure 9:
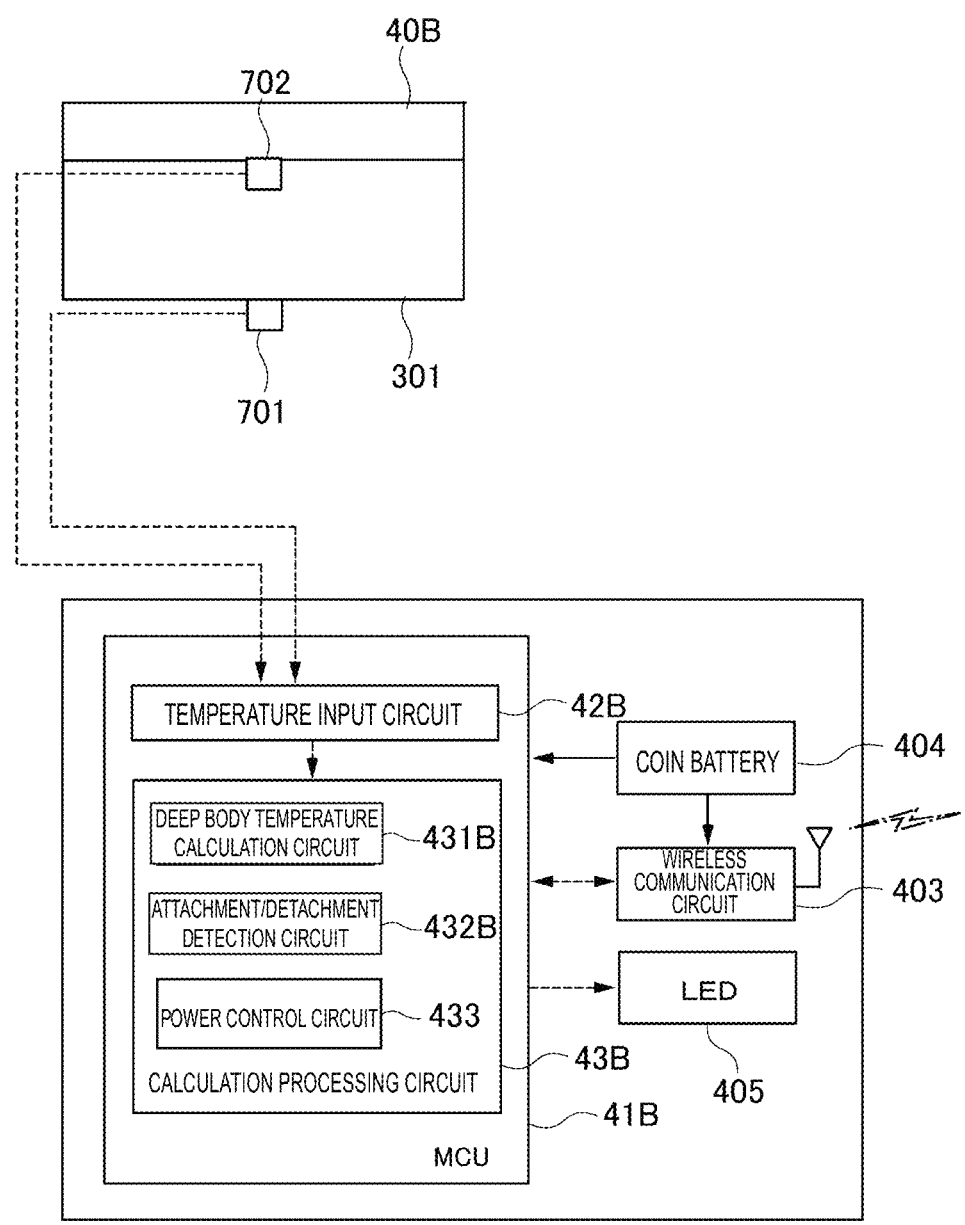
FIG. 9 is a block diagram showing the functional configuration of a processing circuit that is a component of a sticking-type deep body thermometer according to a modification.

Here, in the above-described embodiment, the temperature detecting circuit includes two heat flux lines; however, when a thermal resistance RB of a human body is able to be acquired, the temperature detecting circuit may include a single heat flux line. A sticking-type deep body thermometer 1B according to a modification will be described with reference to FIG. 9. FIG. 9 is a block diagram showing the functional configuration of a processing circuit 41B that is a component of the sticking-type deep body thermometer 1B according to the modification.

When the thermal resistance RB of a user (human body) is known, it is possible to calculate (estimate) a deep body temperature by using the first temperature T1 and the second temperature T2. More specifically, where the deep body temperature of the human body is Tb, the detected temperature of the first temperature sensor 701 is T1, the detected temperature of the second temperature sensor 702 is T2, an equivalent thermal resistance from a human body deep part to a body surface is RB, and an equivalent thermal resistance in the thickness direction of the thermal resistor 301 is RpA, the deep body temperature Tb is expressed by the following expression (2).

$$Tb=T2+\{(RB+RpA)/RpA\}(T1-T2) \quad (2)$$

Therefore, when the thermal resistance RB of the human body is known, or, for example, a general (standard) thermal resistance value is set as the thermal resistance RB of the human body, a deep body temperature Tb is obtained from the temperature T1 detected by the first temperature sensor 701 and the temperature T2 detected by the second temperature sensor 702.

In this case, an attachment/detachment detection circuit 432B detects the attachment and detachment of the deep body thermometer 1 in accordance with the temperature difference (T1−T2) between the first temperature T1 and the second temperature T2 and/or the temperature rate of change (ΔT1) of the first temperature T1.

More specifically, the attachment/detachment detection circuit 432B determines that attachment or detachment of the deep body thermometer 1 has occurred when, within a predetermined time (within, for example, 20 seconds), the sign of the temperature difference (T1−T2) between the first temperature T1 and the second temperature T2 is inverted and the absolute value (|T1−T2|) of the temperature difference becomes greater than or equal to a predetermined threshold value (which corresponds to a first threshold value). The details of the detection method are as described above, so the detailed description is omitted here.

The attachment/detachment detection circuit 432B is also capable of determining that attachment or detachment of the deep body thermometer 1 has occurred when the absolute value of the temperature rate of change (ΔT1) of the first temperature T1 becomes greater than or equal to a predetermined threshold value (which corresponds to a second threshold value).

Then, the attachment/detachment detection circuit 432B desirably determines that attachment or detachment of the deep body thermometer 1 has occurred when the absolute value of the temperature rate of change (ΔT1) of the first temperature T1 becomes greater than or equal to a predetermined threshold value (second threshold value) and the absolute value of the temperature rate of change (ΔT2) of the second temperature T2 becomes greater than or equal to a predetermined threshold value (third threshold value). It is desirable that the second threshold value be set to a value greater than the third threshold value.

As described in detail above, according to the present embodiment, a deep body temperature is estimated in accordance with the first temperature T1, the second temperature T2, the third temperature T3, and the fourth temperature T4, and the attachment and detachment of the deep body thermometer 1 are detected in accordance with at least any one of the temperature difference (T1−T2) between the first temperature T1 and the second temperature T2, the temperature difference (T3−T4) between the third temperature T3 and the fourth temperature T4, the temperature difference (T3−T1) between the third temperature T3 and the first temperature T1, the temperature rate of change (ΔT1) of the first temperature T1, and the temperature rate of change (ΔT3) of the third temperature T3. Here, the first temperature T1 is a temperature at the surface, adjacent to the sticking member 60, of the first thermal resistor 301 (that is, the living body-side temperature), and the second temperature T2 is a temperature at the surface on the back side of the first thermal resistor 301 (that is, an outside air-side temperature). Similarly, here, the third temperature T3 is a temperature at the surface adjacent to the sticking member 60, of the second thermal resistor 302 (that is, the living body-side temperature), and the fourth temperature T4 is a temperature at the surface on the back side of the second thermal resistor 302 (that is, an outside air-side temperature). The thermal resistance value of the second thermal resistor 302 is set so as to be higher than the thermal resistance value of the first thermal resistor 301. Therefore, when, for example, a body temperature is higher than an outside air temperature, T3>T1>T2≈T4 when the deep body thermometer 1 is stuck to (mounted on or attached to) the living body (body surface). At the time of attachment or detachment, T1 and T3 (the body surface-side temperatures) are greater in temperature change and higher in temperature rate of change than T2 and T4. Therefore, by using the characteristics of such T1, T2, T3, and T4, the relation between T1 and T2, the relation between T3 and T4, and the relation between T3 and T1, it is possible to detect the attachment and detachment of the deep body thermometer 1 in accordance with at least any one of a difference (T1−T2) between the first temperature T1 and the second temperature T2, a temperature difference (T3−T4) between the third temperature T3 and the fourth temperature T4, a temperature difference (T3−T1) between the third temperature T3 and the first temperature T1, a temperature rate of change (ΔT1) of the first temperature T1, and a temperature rate of change (ΔT3) of the third temperature. When a body temperature is lower than an outside air temperature, the high/low (magnitude) relation between T1 and T2 and the high/low (magnitude) relation between T3 and T4 are inverted; however, it is possible to similarly detect attachment and detachment. As a result, in the deep body thermometer that is stuck to a living body to measure a deep body temperature is capable of detecting attachment and detachment without adding a new dedicated component (another sensor or the like), that is, without increasing cost.

More specifically, according to the present embodiment, it may be determined that attachment or detachment of the deep body thermometer 1 has occurred when, within a predetermined time, the sign of the temperature difference (T1−T2) between the first temperature T1 and the second temperature T2 is inverted and the absolute value of the temperature difference becomes greater than or equal to a predetermined threshold value (fifth threshold value) and/or the sign of the temperature difference (T3−T4) between the third temperature T3 and the fourth temperature T4 is inverted and the absolute value of the temperature difference becomes greater than or equal to a predetermined threshold value (sixth threshold value).

Similarly, according to the present embodiment, it may be determined that attachment or detachment of the deep body thermometer 1 has occurred when, within a predetermined time, the sign of the temperature difference (T3−T1) between the third temperature T3 and the first temperature T1 is inverted and the absolute value of the temperature difference becomes greater than or equal to a predetermined threshold value (fourth threshold value).

In addition, according to the present embodiment, it may be determined that attachment or detachment of the deep body thermometer 1 has occurred when, within a predetermined time, the absolute value of the temperature rate of change ($\Delta T3$) of the third temperature T3 becomes greater than or equal to a predetermined threshold value (sixth threshold value) and/or when the absolute value of the temperature rate of change ($\Delta T1$) of the first temperature T1 becomes greater than or equal to a predetermined threshold value (second threshold value). When a body temperature and an outside air temperature are relatively close to each other, it is possible to further enhance detection accuracy as compared to the case where a temperature difference is used.

Furthermore, according to the present embodiment, it may be determined that attachment or detachment of the deep body thermometer 1 has occurred when, within a predetermined time, the absolute value of the temperature rate of change ($\Delta T3$) of the third temperature T3 becomes greater than or equal to a predetermined threshold value (seventh threshold value) and the absolute value of the temperature rate of change ($\Delta T4$) of the fourth temperature T4 becomes greater than or equal to a predetermined threshold value (eighth threshold value) and/or when the absolute value of the temperature rate of change ($\Delta T1$) of the first temperature T1 becomes greater than or equal to a predetermined threshold value (second threshold value) and the absolute value of the temperature rate of change ($\Delta T2$) of the second temperature T2 becomes greater than or equal to a predetermined threshold value (third threshold value).

According to the present embodiment, it is assumed (estimated) that the deep body thermometer 1 is attached to the living body and attachment/detachment detection is started when a predetermined time (for example, 10 minutes) or longer has elapsed after the power is turned on or after a measurement is started. Therefore, after that (subsequently), when attachment or detachment of the deep body thermometer 1 is detected, it may be determined that the deep body thermometer 1 is detached. In other words, it is possible to distinguish attachment and detachment of the deep body thermometer 1 from each other.

According to the present embodiment, it is determined that the deep body thermometer 1 is attached when the temperature difference (T3−T1) between T3 and T1, the temperature difference (T3−T4) between T3 and T4, or the temperature difference (T1−T2) between T1 and T2 has exceeded a predetermined threshold value for a predetermined time (for example, 10 minutes). Therefore, it is possible to distinguish attachment and detachment of the deep body thermometer 1 from each other.

According to the present embodiment, it is possible to detect (determine) attachment and detachment with a relatively simple calculation, so it is possible to reduce processing load on attachment/detachment detection. Also, according to the present embodiment, a temperature difference of the two temperature sensors 70 is used for attachment/detachment detection, so, even when noise of the same phase is superimposed on the outputs of the two temperature sensors 70, the noises are cancelled out, with the result that noise toughness is improved.

According to the present embodiment, when attachment or detachment of the deep body thermometer 1 is detected, attachment/detachment information indicating that the deep body thermometer 1 is attached or detached is transmitted to the management device and management system 3. Therefore, when the deep body thermometer 1 is detached from the body surface, it is possible to inform the detachment.

According to the present embodiment, when attachment or detachment of the deep body thermometer 1 is detected, attachment/detachment information is provided to the supervisor's mobile terminal 5 via the management device and management system 3. Therefore, when the deep body thermometer 1 is detached from the body surface, it is possible to inform the supervisor of the detachment.

According to the present embodiment, the deep body thermometer 1 shifts into a low power consumption mode (sleep mode) or turns off the power when it is determined that the deep body thermometer 1 is detached from the living body. Therefore, when the deep body thermometer 1 is detached, low power consumption is achieved by stopping part of the functions or turning off the power.

According to the above-described modification, with the single heat flow deep body thermometer 1B as well, it is possible to similarly detect attachment and detachment.

The embodiment of the present invention is described above; however, the present invention is not limited to the above-described embodiment and may be modified in various forms. For example, a sensor that detects an outside air temperature may be further provided. Outside air temperature data may be received from the management device and management system 3, the mobile terminal 5, or the like, and detachment and attachment of the deep body thermometer 1 may be configured to be distinguished from each other. Furthermore, attachment and detachment may be detected by using some of the above-described attachment/detachment detection methods in combination.

The present invention is suitably usable in, for example, a hospital system, a construction site, an elderly facility system, or the like.

REFERENCE SIGNS LIST 1,1B deep body thermometer
3 management device and management system
5 mobile terminal
10 upper exterior body
15 body temperature measurement unit
20 lower exterior body
30 thermal resistor layer
301 first thermal resistor
302 second thermal resistor
301a, 302a through-hole 40 wiring substrate
41, 41B processing circuit
42, 42B temperature input circuit
43, 43B calculation processing circuit
431, 431B deep body temperature calculation circuit
432, 432B attachment/detachment detection circuit
433, 433B power control circuit
403 wireless communication circuit
404 coin battery
405 LED
406 power switch
407 FPC connector
50 flexible substrate
60 sticking member
601 first adhesion layer
602 second adhesion layer
603 vent layer
60a, 60b through-hole
701, 702, 703, 704 temperature sensor
80 lining member
80a through-hole
90 shock-absorbing member
90a through-hole
95 battery holder

The invention claimed is:

1. A sticking-type deep body thermometer comprising:
a thermometer body;
a sticking member having an adhesive property on a bottom surface of thermometer body;
a first thermal resistor having a predetermined thermal resistance and disposed substantially parallel to the sticking member;
a first temperature sensor configured to detect a first temperature at a first surface of the first thermal resistor adjacent to the sticking member;
a second temperature sensor configured to detect a second temperature at a second surface of the first thermal resistor opposite the first surface;
a deep body temperature detection circuit configured to estimate a deep body temperature based on the first temperature and the second temperature; and
an attachment/detachment sensor configured to detect attachment and detachment of the sticking-type deep body thermometer, wherein the attachment/detachment sensor determines that attachment or detachment of the sticking-type deep body thermometer has occurred when, within a predetermined time, a sign of a temperature difference between the first temperature and the second temperature is inverted and an absolute value of the temperature difference becomes greater than or equal to a first threshold value.

2. The sticking-type deep body thermometer according to claim 1, further comprising a transmission circuit configured to transmit attachment/detachment information indicating that the sticking-type deep body thermometer has been attached or detached when attachment or detachment of the sticking-type deep body thermometer has been detected.

3. The sticking-type deep body thermometer according to claim 1, further comprising a power control circuit configured to shift the sticking-type deep body thermometer into a low power consumption mode or turn off a power of the sticking-type deep body thermometer when detachment of the sticking-type deep body thermometer has been determined.

4. The sticking-type deep body thermometer according to claim 1, wherein the attachment/detachment sensor starts attachment/detachment detection when a predetermined time has elapsed after a power is turned on or after a measurement is started.

5. A sticking-type deep body thermometer comprising:
a thermometer body;
a sticking member having an adhesive property on a bottom surface of thermometer body;
a first thermal resistor having a predetermined thermal resistance and disposed substantially parallel to the sticking member;
a first temperature sensor configured to detect a first temperature at a first surface of the first thermal resistor adjacent to the sticking member;
a second temperature sensor configured to detect a second temperature at a second surface of the first thermal resistor opposite the first surface;
a deep body temperature detection circuit configured to estimate a deep body temperature based on the first temperature and the second temperature; and
an attachment/detachment sensor configured to detect attachment and detachment of the sticking-type deep body thermometer, wherein the attachment/detachment sensor determines that attachment or detachment of the sticking-type deep body thermometer has occurred when, within a predetermined time, an absolute value of a temperature rate of change of the first temperature becomes greater than or equal to a second threshold value.

6. The sticking-type deep body thermometer according to claim 5, further comprising a transmission circuit configured to transmit attachment/detachment information indicating that the sticking-type deep body thermometer has been attached or detached when attachment or detachment of the sticking-type deep body thermometer has been detected.

7. The sticking-type deep body thermometer according to claim 5, further comprising a power control circuit configured to shift the sticking-type deep body thermometer into a low power consumption mode or turn off a power of the sticking-type deep body thermometer when detachment of the sticking-type deep body thermometer has been determined.

8. The sticking-type deep body thermometer according to claim 5, wherein the attachment/detachment sensor starts attachment/detachment detection when a predetermined time has elapsed after a power is turned on or after a measurement is started.

9. A sticking-type deep body thermometer comprising:
a thermometer body;
a sticking member having an adhesive property on a bottom surface of thermometer body;
a first thermal resistor having a predetermined thermal resistance and disposed substantially parallel to the sticking member;
a first temperature sensor configured to detect a first temperature at a first surface of the first thermal resistor adjacent to the sticking member;
a second temperature sensor configured to detect a second temperature at a second surface of the first thermal resistor opposite the first surface;
a deep body temperature detection circuit configured to estimate a deep body temperature based on the first temperature and the second temperature; and
an attachment/detachment sensor configured to detect attachment and detachment of the sticking-type deep body thermometer, wherein the attachment/detachment sensor determines that attachment or detachment of the sticking-type deep body thermometer has occurred when, within a predetermined time, an absolute value of a temperature rate of change of the first temperature becomes greater than or equal to a second threshold value and an absolute value of a temperature rate of change of the second temperature becomes greater than or equal to a third threshold value.

10. The sticking-type deep body thermometer according to claim 9, further comprising a transmission circuit configured to transmit attachment/detachment information indicating that the sticking-type deep body thermometer has been attached or detached when attachment or detachment of the sticking-type deep body thermometer has been detected.

11. The sticking-type deep body thermometer according to claim 9, further comprising a power control circuit configured to shift the sticking-type deep body thermometer into a low power consumption mode or turn off a power of the sticking-type deep body thermometer when detachment of the sticking-type deep body thermometer has been determined.

12. The sticking-type deep body thermometer according to claim 9, wherein the attachment/detachment sensor starts attachment/detachment detection when a predetermined time has elapsed after a power is turned on or after a measurement is started.

13. A sticking-type deep body thermometer comprising:
a thermometer body;
a sticking member having an adhesive property on a bottom surface of thermometer body;
a first thermal resistor having a predetermined thermal resistance and disposed substantially parallel to the sticking member;
a first temperature sensor configured to detect a first temperature at a first surface of the first thermal resistor adjacent to the sticking member;
a second temperature sensor configured to detect a second temperature at a second surface of the first thermal resistor opposite the first surface;
a deep body temperature detection circuit configured to estimate a deep body temperature based on the first temperature and the second temperature; and
an attachment/detachment sensor configured to detect attachment and detachment of the sticking-type deep body thermometer in accordance with a magnitude relation between the deep body temperature and an outside air temperature.

14. The sticking-type deep body thermometer according to claim 13, further comprising a transmission circuit configured to transmit attachment/detachment information indicating that the sticking-type deep body thermometer has been attached or detached when attachment or detachment of the sticking-type deep body thermometer has been detected.

15. The sticking-type deep body thermometer according to claim 13, further comprising a power control circuit configured to shift the sticking-type deep body thermometer into a low power consumption mode or turn off a power of the sticking-type deep body thermometer when detachment of the sticking-type deep body thermometer has been determined.

16. The sticking-type deep body thermometer according to claim 13, wherein the attachment/detachment sensor starts attachment/detachment detection when a predetermined time has elapsed after a power is turned on or after a measurement is started.

\* \* \* \* \*